(12) United States Patent
Keng et al.

(10) Patent No.: US 9,321,866 B2
(45) Date of Patent: Apr. 26, 2016

(54) POLYMER MONOLITHS FOR SOLVENT EXCHANGE IN CONTINUOUS FLOW MICROFLUIDIC DEVICE

(71) Applicant: THE REGENTS OF THE UNIVERSITY OF CALIFORNIA, Oakland, CA (US)

(72) Inventors: Pei Yuin Keng, Los Angeles, CA (US); Rehana Ismail, Los Angeles, CA (US); Ariella Machness, Los Angeles, CA (US); Kyoung-Joo Jenny Park, Los Angeles, CA (US)

(73) Assignee: THE REGENTS OF THE UNIVERSITY OF CALFIORNIA, Oakland, CA (US)

( * ) Notice: Subject to any disclaimer, the term of this patent is extended or adjusted under 35 U.S.C. 154(b) by 0 days.

(21) Appl. No.: 14/406,202

(22) PCT Filed: Jun. 11, 2013

(86) PCT No.: PCT/US2013/045241
§ 371 (c)(1),
(2) Date: Dec. 5, 2014

(87) PCT Pub. No.: WO2013/188446
PCT Pub. Date: Dec. 19, 2013

(65) Prior Publication Data
US 2015/0152206 A1 Jun. 4, 2015

Related U.S. Application Data

(60) Provisional application No. 61/658,292, filed on Jun. 11, 2012.

(51) Int. Cl.
| | | |
|---|---|---|
| *C08F 2/46* | (2006.01) | |
| *C08G 61/04* | (2006.01) | |
| *C08F 212/14* | (2006.01) | |
| *A61B 5/15* | (2006.01) | |
| *B01J 19/00* | (2006.01) | |
| *C07B 59/00* | (2006.01) | |
| *C07H 13/04* | (2006.01) | |
| *C08F 236/20* | (2006.01) | |
| *A61B 5/151* | (2006.01) | |

(52) U.S. Cl.
CPC ............. *C08F 212/14* (2013.01); *A61B 5/1405* (2013.01); *A61B 5/1411* (2013.01); *A61B 5/1514* (2013.01); *A61B 5/150099* (2013.01); *A61B 5/150229* (2013.01); *B01J 19/0093* (2013.01); *C07B 59/005* (2013.01); *C07H 13/04* (2013.01); *C08F 236/20* (2013.01); *A61B 5/150022* (2013.01); *A61B 5/15113* (2013.01); *A61B 5/15117* (2013.01); *B01J 2219/00831* (2013.01); *B01J 2219/00846* (2013.01); *B01J 2219/00905* (2013.01); *B01J 2219/00943* (2013.01)

(58) Field of Classification Search
CPC ... C08F 212/14; C08F 236/20; C07B 59/005; B01J 19/0093; B01J 2219/00831; B01J 2219/00943; B01J 2219/00846; B01J 2219/00905; C07H 13/04; A61B 5/1405; A61B 5/150099; A61B 5/15113; A61B 5/1411; A61B 5/1514; A61B 5/150229; A61B 5/150022; A61B 5/15117
USPC .................................. 522/185, 184, 1; 520/1
See application file for complete search history.

(56) References Cited

U.S. PATENT DOCUMENTS

| | | | |
|---|---|---|---|
| 6,887,384 B1 * | 5/2005 | Frechet | .................... B01J 20/26 210/198.2 |
| 2004/0101442 A1 | 5/2004 | Frechet et al. | |
| 2008/0318334 A1 | 12/2008 | Robotti | |
| 2010/0069600 A1 * | 3/2010 | Morelle | ................... G21G 4/08 528/271 |
| 2011/0028669 A1 | 2/2011 | Robotti | |

FOREIGN PATENT DOCUMENTS

| | | |
|---|---|---|
| EP | 1933330 A1 | 6/2008 |
| WO | WO 2009003251 | 8/2009 |

OTHER PUBLICATIONS

Lu, S.Y. et al., Micro-reactors for PET Tracer Labeling, in PET Chemistry A. P. Schubiger, L. Lehmann, M. Friebe, Eds. (Ernst Schering Foundation Symposium Proceedings, 2007), vol. 64, pp. 271-287.

(Continued)

*Primary Examiner* — Ling Choi
*Assistant Examiner* — Jessica E Whiteley
(74) *Attorney, Agent, or Firm* — Vista IP Law Group LLP

(57) ABSTRACT

The present disclosure relates to the novel multistep procedure for preparation of polymer monoliths for use in solvent exchange, such as methods to exchange and activate fluoride ions on a flow through microfluidic chip for subsequent chemical synthesis. Methods according to the present disclosure include the application of such microfluidic platforms for rapid F18 radiosynthesis on a flow through microfluidic chip with high efficiency, followed by a subsequent nucleophilic fluorination reaction. Various other methods of exchanging and activating fluoride ions on a flow through microfluidic chip are also disclosed. Methods incorporating features of the present invention can be applicable to any flow through microfluidic device in any field, such as radiosyntheses, chemical syntheses, concentration of ions for environmental analyzes and sample preparation such as concentrating minute amounts of analyte to improve the downstream detection.

17 Claims, 5 Drawing Sheets

(56) References Cited

OTHER PUBLICATIONS

Lasne, M.G. et al., Chemistry of B+-Emitting Compounds Based on Fluoride-18, in Contrast Agents II, W. Krause, Ed. (Springer Berlin Heidelberg, Berlin, Heidelberg, 2002), vol. 222, pp. 201-258.
Phelps, M. E., PET: The Merging of Biology and Imaging into Molecular Imaging (Springer, 2004).
Keng, P. Y. et al., Emerging Technologies for Decentralized Production of PET Tracers, in Positron Emission Tomography-Current Clinical and Research Aspects C.H. Hsieh, Ed. (InTech, 2012).
Elizarov, A. M. et al., Microreactors for radiopharmaceutical synthesis, Lab on Chip, 2009, 9, 1326-1333.
Gillies, J. M. et al., Microfluidic reactor for the radiosynthesis of PET radiotracers, Applied Radiation and Isotopes 64 (2006) 325-332.
Wester, H. J. et al., Fast and repetitive in-capillary production of [18F]FDG, Eur J Nucl Med Mol Imaging (2009) 36:653-658.
Pascali, G. et al., Microfluidic Approach for Fast Labeling Optimization and Dose-on-Demand Implementation, Nuc. Med. Biol. 37 (2010), 547-555.
Keng, P.Y. et al., Micro-chemical synthesis of molecular probes on an electronic microfluidic device, PNAS, Jan. 17, 2012, vol. 109, No. 3. 690-695.
Wiles, C. et al., Continuous Flow Reactors, a Tool for the Modern Synthetic Chemist. Eur. J. Org. Chern., 2008, 1655-1671.
Bouvet, V. R. et al., Synthesis of hypoxia imaging cell 1-(5-deoxy-5-fluoro-a-D-arabinofuranosyl)-2-nitroimidazole using microfluidic technology, Nuc. Med. Biol. 38 (2011) 235-245.
Xie, S. et al., Porous Polymer Monoliths: Preparation of Sorbent Materials with High-Surface Areas and Controlled Surface Chemistry for High-Throughput, Online, Solid• Phase Extraction of Polar Organic Compounds, Chem. Mater. 1998, 10, 4072-4078.
Walsh, Z. et al., Visible light initiated polymerization of styrenics monolithic stationary phases using 470 nm light emitting diode arrays, J. Sep. Sci. 2010, 33, 61-66.
Aerts, J. et al., Fast production of highly concentrated reactive [18F]fluoride for aliphatic and aromatic nucleophilic radiolabeling, Tetrahedron Letters 51 (2010) 64-66.
Lee, C. C. et al., Multistep Synthesis of a Radiolabeled Imaging Probe Using Integrated Microfluidics, Science 310, 1793 (2005).
De Leonardis, F. et al., On-chip pre-concentration and complexation of [18F]fluoride ions via regenerable anion exchange particles for radiochemical synthesis of Positron Emission Tomography tracers, Journal of Chromatography A, 1218 (2011) 4714-4719.
Saiki, H. et al., Electrochemical concentration of no-carrier-added [18F]fluoride from [18O]water in a disposable microfluidic cell for radiosynthesis of 18F-labeled radiopharmaceuticals, Applied Radiation and Isotopes 68 (2010) 1703-1708.
Wong, R. et al., Reactivity of electrochemically concentrated anhydrous [18F]fluoride for microfluidic radiosynthesis of 18F-labeled compounds, Applied Radiation and Isotopes 70 (2012) 193-199.
Galindo, F. et al., A Sensitive Colorimetric Method for the Study of Polystyrene Merrifield Resins and Chloromethylated Macroporous Monolithic Polymers, J. Comb. Chem. 2004, 6, 859-861.
Lee, E. et al., A Fluoride-Derived Electrophilic Late-Stage Fluorination Reagent for PET Imaging, Science 334, 639 (2011).
Mair, D. A. et al., Use of photopatterned porous polymer monoliths as passive micromixers to enhance mixing efficiency of on-chip labeling reactions, Lab Chip, Apr. 7, 2009; 9(7):877-883.
PCT International Preliminary Report on Patentability (Chapter I of the Patent Cooperation Treaty) for PCT/US2013/045241, Applicant: The Regents of the University of California, Form PCT/IB/326 and 373, dated Dec. 24, 2014 (9pages).
PCT International Search Report for PCT/US2013/045241, Applicant: The Regents of the University of California, Form PCT/ISA/210 and 220, Oct. 18, 2013 (5 pages).
PCT Written Opinion of the International Search Authority for PCT/US2013/045241, Applicant: The Regents of the University of California, Form PCT/ISA/237, Oct. 18, 2013 (7pages).

* cited by examiner

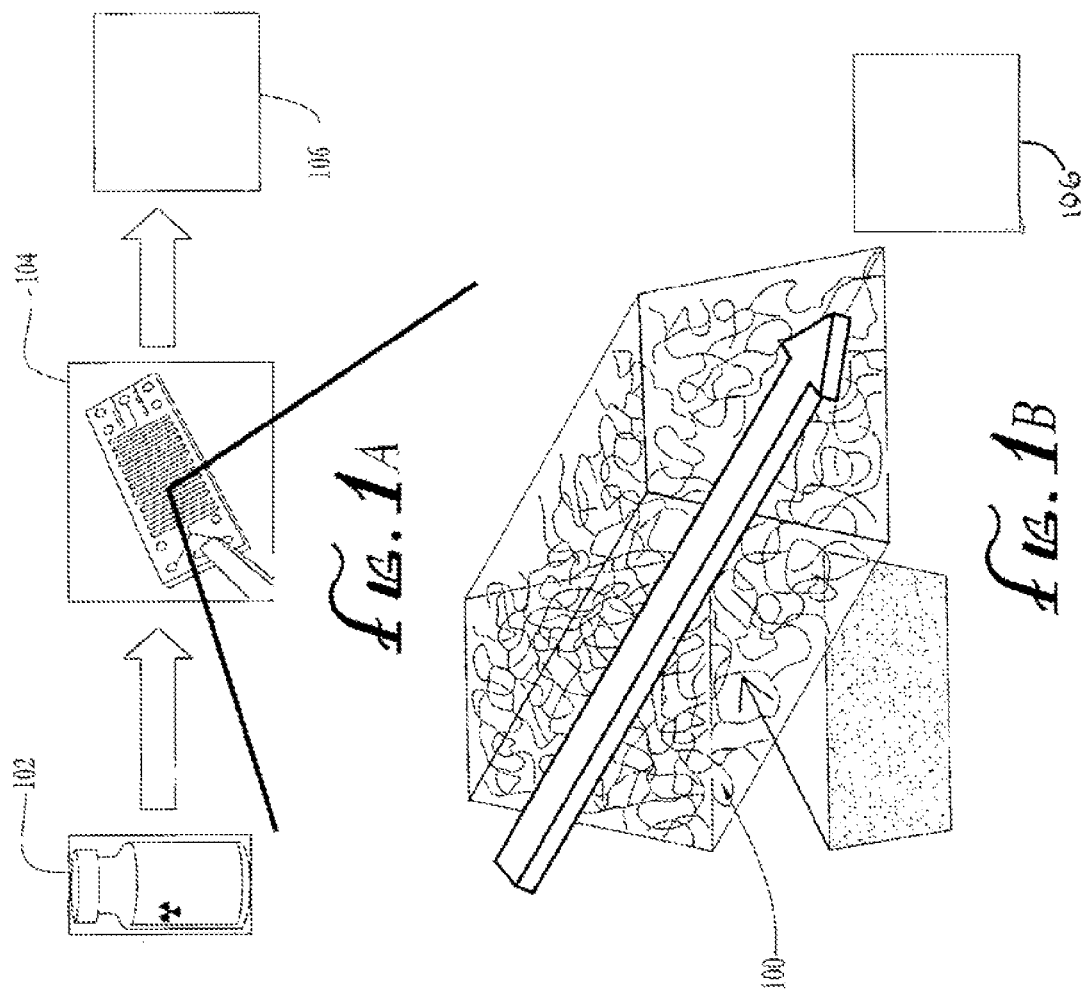

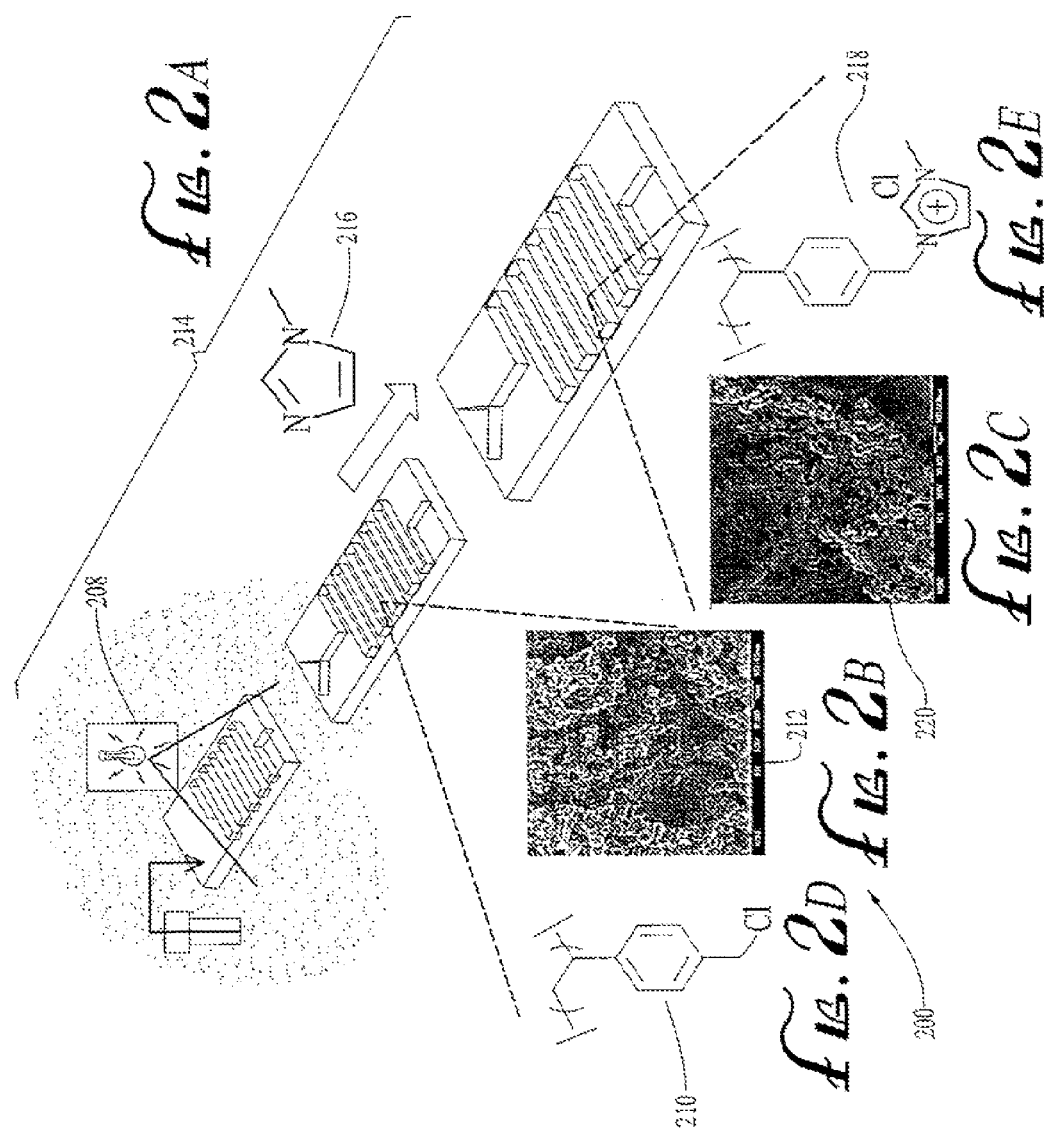

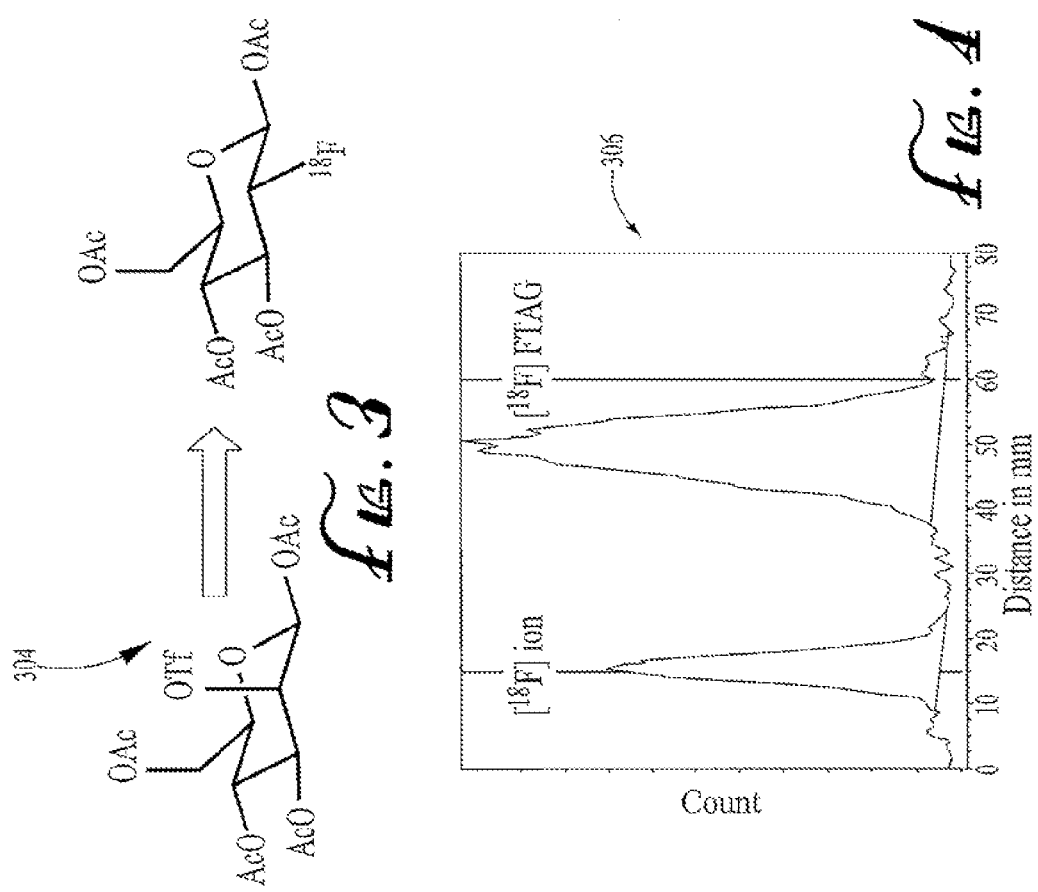

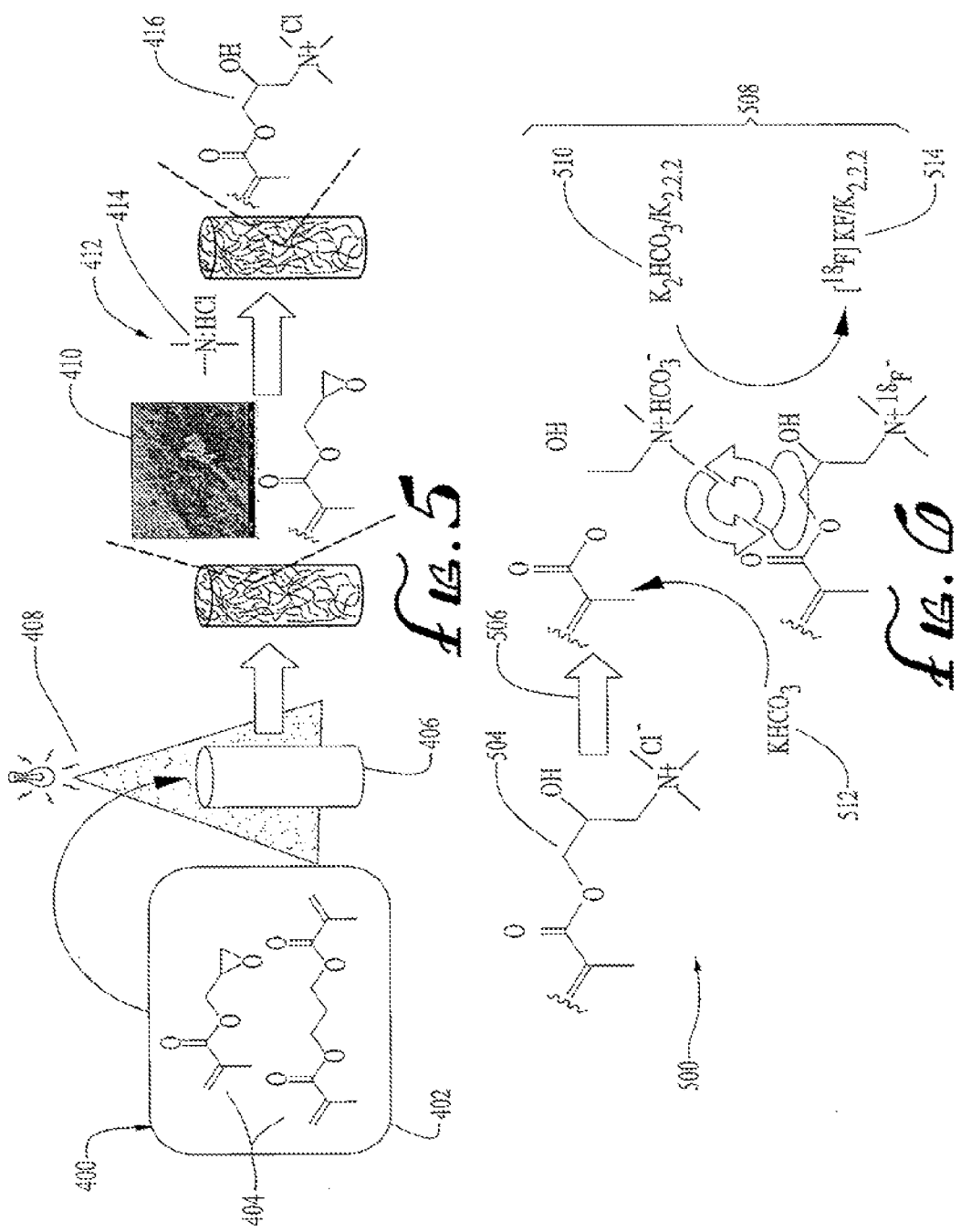

POLYMER MONOLITHS FOR SOLVENT EXCHANGE IN CONTINUOUS FLOW MICROFLUIDIC DEVICE

CROSS REFERENCE TO RELATED APPLICATIONS

This Application is a U.S. National Stage filing under 35 U.S.C. 371 of PCT Patent Application No. PCT/US2013/045241, filed Jun. 11, 2013, which claims priority to U.S. Provisional Patent Application No. 61/658,292, filed on Jun. 11, 2012. The contents of the aforementioned applications are incorporated by reference herein. Priority is expressly claimed in accordance with 35 U.S.C. 119, 120, 365 and 371 and any other applicable statutes.

BACKGROUND OF THE INVENTION

1. Field of the Invention

The present disclosure relates to the novel preparation of polymer monoliths for solvent exchange in a multistep reaction, for example, a method for the exchange and activation of fluoride ions on a flow through microfluidic chip for subsequent chemical synthesis.

2. Description of the Related Art

Methods in the current state of the art relating to the exchange and activation of fluoride ions typically utilize micrometer sized beads or resins (50-100 um) as a solid phase support with different functionalities some methods result in the release of a $[^{18}F]$fluoride ion in as little as 1% water in acetonitrile and further demonstrate radiofluorination of common substrates with moderate fluorination efficiency without performing additional azeotropic distillation. Other organizations have reported functionalizing the conventional beads with a long alkyl chain of quaternary ammonium which enables efficient recovery of the $[^{18}F]$fluoride ion in low water content organic solution. This is set forth in J. Aerts et al., *Fast Production of Highly Concentrated Reactive [18F] Fluoride for Aliphatic and Aromatic Nucleophilic Radiolabeling, Tetrahedron Letters* 51, 64 (2010), which is hereby incorporated herein in its entirety by reference.

The above described methods demonstrated successful radiofluorination of several substrates as a model system with moderate yield without performing additional drying steps. However, both methods utilized micron-sized beads with large bed volume packed in a cartridge format, which are conventionally used in macroscale synthesis. Such an approach can not be efficiently downscaled to a microfluidic platform due to the limited numbers of beads that can be placed in microchannels and thus a limited availability of surface active sites for ion exchange. For example, one of the major limitations of fluoride ion concentration utilizing a microfluidic chip using conventional resins is the inability to trap a sufficient number of radioactive fluoride ions within the micron-sized channels. Such a convention method is set forth in C. C. Lee et. al., *Multistep Synthesis of a Radiolabed Imaging Probe Using integrated Microfluidics*, Science 310, 179.3 (2005), which is hereby incorporated herein in its entirety by reference. The procedure and techniques using microchips as reported here can overcome such challenges.

In the area of microfluidic devices for chemical synthesis, the state of the art had previously involved solid supports utilizing the immobilization of micrometer sized resin within microfluidic channels for various applications such as biochemical transformation, catalytic reactions and solid phase extraction. More recently, the development of polymeric monolith materials have demonstrated enhanced performance over their resin counterparts because of the polymeric monolith's unique characteristics, such as ease of preparation, versatile chemistries and functionalities, controlled surface area, large through pores and high hydrodynamic flow. A polymer monolith as used herein includes a continuous polymer bed, macroporous polymer membranes, continuous polymer rods, porous silica rods, a polymer continuous column support, the specifically defined materials and monolith embodiments described herein and or any polymeric structure constituting or acting as a single, often rigid, uniform whole.

Specifically for microfluidic applications, the number of loading sites or total active surface area is extremely critical in determining the yield and efficiencies. For example, scientists at the University of Hull packed 60-100 μm sized polystyrene beads functionalized with bicarbonate anions within a microfluidic chip with dimensions of 30,000 μm×5,000 μm×250 μm. This is set forth in F. De Leonardis et al., *On-Chip Pre-Concentration and Complexation of [18F] Fluoride Ions via Regenerable Anion Exchange Particles for Radiochemical Synthesis of Positron Emission Tomography Tracers*, Journal of Chromatography A, 1218, 4714 (2011), which is hereby incorporated herein in its entirety by reference. Large dimension microfluidic channels are needed to facilitate packing sufficient numbers of beads (with sufficient surface area) for fluoride ion trapping. Due to the large bead volume, an average of 500 μL of phase transfer catalyst solution is needed to efficiently elute the totality of fluoride ions from the polymer support. This methodology yielded only a 2-fold volume concentration (1000 μL from the cyclotron water to 500 μL of the pre-concentrated fluoride ion). While such volume is sufficient for most macroscale synthesis, the 500 μL of radioactivity cannot be efficiently loaded to a batch microfluidic device for radiosynthesis (average reaction volume: 5-20 μL).

Another flow through microfluidic method for concentrating and drying of $[^{18}F]$ ions is via an electrochemical method, which relies on electrical potential to trap the negatively charged fluoride ion onto one of the electrodes. The $[^{18}F]$ fluoride is then released in an aprotic solvent by reversing the applied potential for subsequent radiofluorination reaction. Such methods are further set forth and described in detail in the following: 1) H. Saiki et al, *Electrochemical Concentration of No-Carrier-Added [18F]Fluoride from [18O]Water in a Disposable Microfluidic Cell for Radiosynthesis of 18F-Labeled Radiopharmaceuticals*, Applied Radiation and Isotopes, 68, 1703 (2010); 2) R. Wong et al., *Reactivity of Electrochemically Concentrated Anhydrous [18F]Fluoride for Microfluidic Radiosynthesis of 18F-Labeled Compounds*, Applied Radiation and Isotopes 70,193 (2012); 3) J. I. Morelle, et al. ED. (2008), vol. EP20060447128; all three of said documents hereby incorporated herein in their entirety by reference. Another example of such methods is the demonstrated successful radiofluorination of common positron emission tomography (PET) probes by after electrochemical trapping of the fluoride ion. Said system relies on the ability to prepare an anhydrous phase transfer catalyst, such as a cryptand, for example, Kryptofix® and potassium bicarbonate ($K_{2.2.2}/KHCO_3$) in acetonitrile to release the trapped fluoride from the electrochemical cell. Such an electrochemical platform requires high voltage and other electrical auxiliaries for operation, and thus may not be easily integrated to existing flow through chemistry.

The unstable $[^{18}F]$fluorine isotope plays an important role in radiopharmaceuticals as an ideal probe for positron emission tomography (PET) imaging. PET imaging is an in-vivo, non-invasive imaging technique that uses radiolabelled compounds (in tracer quantities) to measure biochemical, biological, and pharmaceutical processes with high sensitivity. Examples of PET imaging processes are set forth in M. E. Phelps, *PET: Molecular Imaging and Its Biological Applications* (Springer, 2004), which is hereby incorporated herein in its entirety by reference.

This powerful imaging technique has enabled biologists and physicians to diagnose emergence of cancer or other diseases at an early stage by identifying biological changes and to differentiate between benign and malignant lesions to improve prognosis and lower the cost of therapy, personalizing therapies and stage the effectiveness of therapeutic methods, thus increasing the rate of survival, and developing effective drugs and therapeutic methods to prevent and cure cancer.

Fluorine-18 possesses many desirable properties such as the strong and stable C—F bond and the relatively low energy (max: 0.645 MeV) resulting in a short linear range and thus providing high image resolution. These and other properties of Fluorine-18 are set forth in M. C. Lasne et al., Contrasting Agents II, W. Krause ED. (Springer Berlin Heidelberg, Berlin, Heidelberg, 2002), vol. 222, pp. 201-258, which is hereby incorporated herein in its entirety by reference.

Furthermore, the 109 minute half-life of Fluorine-18 provides sufficient time for the radiolabelled probe generated in one facility to be shipped to other nearby imaging centers and permits longer imaging protocols to investigate processes of slower kinetics.

Due to the efficacy of PET imaging, there has been a drastic increase in the growth of PET imaging in preclinical and clinical research, pharmaceuticals and medical communities. An example of such research is set forth in P. Y. Keng, et al, *Positron Emission Tomography-Current Clinical and Research Aspects* C. H. Hsieh, Ed. (InTech, 2012), which is hereby incorporated herein in its entirety by reference. However, the current bottle-neck in advancing PET imaging is in increasing efficiency and diversity of radiolabeling small molecules and biological compounds.

To date, only a few selected PET probes (i.e.: [$^{18}$F]FDG and [$^{18}$]NaF) are available at centralized radiopharmacies, and the availability of other radiolabeled compounds is severely limited by the cost, speed and efficiency of radiosynthetic method. Recently, microfluidic radiosynthesizers have emerged as a potential microscale radiosynthesizer for on-demand production of individual doses of PET probes as a technological tool in enabling researchers to synthesize both known and new PET probes of interest on demand. An example of this is demonstrated in A. M. Elizarov, Microreactors for Radiopharmaceutical Synthesis, *Lab on a Chip*, 9, 1326 (2009), which is hereby incorporated herein in its entirety by reference In particular, continuous flow microfluidic and capillary microreactor radiosynthesizers have demonstrated remarkable reaction kinetics down to nine seconds to achieve moderate fluorination efficiency of mannose triflate. Examples of such results are set forth in J. M. Gillies et al., *Microfluidic Reactor for the Radiosynthesis of PET Radiotracers*, Applied Radiation and Isotopes 64, 325 (2006), which is hereby incorporated herein in its entirety by reference. Continuous-flow synthesizer platforms have several other advantages, such as the ability to conduct reactions at high temperature and/or high pressure, and to perform multiple optimization reactions in a short time. Examples of these and other advantages are set forth in H. J. Wester, et al, *Fast and Repetitive In-Capillary Production of [18F]FDG*, European Journal of Nuclear Medicine and Molecular Imaging 36, 653 (2008), which is hereby incorporated herein in its entirety by reference.

However, one of the major drawbacks of these previous continuous flow systems is their inability to perform solvent exchange and evaporation, which is one of the most critical processes of nucleophilic fluorination reactions. In these reactions, the radioactive F18-fluoride ion is generated in a cyclotron and then solvated by [18O]H$_2$O. In water, the fluoride ion is inactive in relation to any chemical reaction. Therefore, the first step in a typical F18 radiosynthesis involves the concentration of the F18-fluoride ion, followed by several cycles of azeotropic distillation in the presence of suitable phase transfer catalyst to remove all the water, this process is commonly known as solvent exchange. To date, flow through synthesizer systems rely on other means of evaporation to remove the water from the [$^{18}$]F-/[18O]H$_2$O source, such as integrating to a macroscale synthesizer with an evaporation vessel. The dried and activated [$^{18}$F]F-complex is then transferred to the microfluidic or capillary microreactor for subsequent fluorination steps. Such a flow-through synthesis system is set forth in G. Pascali, et al., Microfluidic Approach for Fast Labeling Optimization and Dose-On-Demand Implementation, Nuc. Med. Biol. 37, 547 (2010), which is hereby incorporated herein in its entirety by reference.

The integration of the milliliter flask reactor to microvolume procedures often resulted in the need to use a large volume of solvent to transfer the radioactive source. The low mass of [$^{18}$F]fluoride often leads to considerable radioactivity losses due to surface adsorption on the walls of the typical Pyrex® vials used in most laboratories. Secondly, the need for an additional macroscale "drying" platform significantly increased the overall size of the radiosynthesizer platform, which defeats the inherent advantages of a compact-sized microreactor. Accordingly there is a need for practical and efficient interfaces for concentrating, drying and activating a non-carrier added (n.c.a.) [$^{18}$F]fluoride solution generated in a cyclotron to provide of microliter volumes for F18-labeled radiopharmaceutical production on microfluidic platforms.

SUMMARY

The present disclosure relates to the novel multistep procedure for preparation of polymer monoliths for use in solvent exchange. For example, this disclosure encompasses methods to exchange and activate fluoride ions on a flow through microfluidic chip, within plastic tubing or silica capillary for subsequent chemical synthesis. One advantage of embodiments incorporating features of the present invention is that methods are disclosed for fabricating a polymer monolithic microfluidic platform for ion concentration, solvent exchange, and activation processes on a single chip. This is the first microfluidic platform that has been demonstrated to perform the multistep processes efficiently. Methods according to the present disclosure include the application of such microfluidic platforms for rapid F18 radiosynthesis on a flow through microfluidic chip with high efficiency, followed by a subsequent nucleophilic fluorination reaction.

Methods incorporating features of the present invention can be applicable to any flow through microfluidic device, tubing, and silica capillary in any field, such as radiosyntheses, chemical syntheses, concentration of ions for environmental analyses and sample preparation such as concentrating minute amounts of analyte to improve the downstream detection. Such methods are also applicable to any flow through capillary platforms or microfluidic platforms, which involve solvent exchange processes, specifically in multistep organic synthesis. Examples of such organic synthesis environments in which methods incorporating features of the present invention can be applied are set forth in S. Y. Lu, et al., *PET Chemistry* A. P. Schubiger, et al. Eds. (Ernst Schering Foundation Symposium Proceedings, 2007), vol. 64, pp. 271-287, which is hereby incorporated herein in its entirety by reference.

Methods incorporating features of the present invention can utilize a functional polymer monolith with high surface area and high permeability within a confined structure to achieve quantitative trapping efficiency. A new method of releasing and recovering the trapped ions from the polymer monolith is also presented in this disclosure. In one embodiment, a mixture of precursor, base and phase transfer catalyst in acetonitrile was used to achieve high and reliable releasing efficiency. Using this mixture of reagents for the subsequent chemical synthesis, a high radiofluorination efficiency and radiochemical yield (RCY) were also demonstrated for various PET probe precursors. This embodiment, combining the precursor and phase transfer catalyst mixture, allow significant reduction in the overall size and footprint of the platform and minimize the use of syringe pump.

The present disclosure provides a novel methodology based on a functional polymer monolith on a continuous flow microfluidic chip to perform fluoride ion concentration, solvent exchange and activation. The methodology presented here could be used to bridge the macro- to the micro-world, specifically in concentrating milliliters to tens of microliter in volume, which is commensurate for application on microfluidic devices. Secondly, the monolithic microfluidic platform could enable solvent exchange and activation of the fluoride ions on the same microfluidic platform. As will be discussed further below, the applicability of this method in the radiofluorination of [$^{18}$F]FTAG (an intermediate precursor of [$^{18}$F]fluorodeoxyglucose) starting from the [$^{18}$F]fluoride ion concentration, activation and fluorination reaction on continuous flow microfluidic chip is shown. Furthermore, this disclosure demonstrates 98% trapping efficiency of fluoride ions in varying volumes (200-1000 uL), which are then activated and released in the [$^{18}$F]fluoride ion activated form to perform the subsequent fluorination reaction.

In some embodiments, the fluorination efficiency of mannose triflate was found to be 91%, without performing additional drying and activation processes. This result showed that the polymer monolithic microfluidic platform is effective in concentrating and releasing the [$^{18}$F]fluoride ion in an activated form for subsequent reaction as the fluorination efficiency is comparable to a standard procedure.

This disclosure further discloses novel methods regarding flow through microfluidic platforms with the capability of performing the solvent exchange process, which was one of the major limitations of previous continuous flow microfluidic devices. To date, flow through glass microreactor platforms are limited to performing chemical synthesis; the number of chemical synthesis steps can typically be increased only by using multiple chips. See, for example, C. Wiles, et al., *Continuous Flow Reactors, a Tool for the Modern Synthetic Chemist*, Eur. J. Org. Chem., 1655 (2008), which is hereby incorporated herein in its entirety by reference.

Embodiments according to the present invention can be applicable to any flow through microfluidic devices in any field such as radiosyntheses, chemical syntheses, concentration of ions for environmental analyses and sample preparation such as concentrating minute amount of analyte to improve the downstream detection. For example, the present invention could be integrated with other commercially available microreactors such as the Advion NanoTek Microfluidic Flow-Chemistry System® (available from Advion, Inc., Ithaca, N.Y.) and the FutureChemistry® synthesis platforms (available from FutureChemistry Holding, BV, The Netherlands), which have gained increasing utilization in research institutes.

For Example, the Advion® system is integrated with a drying box, which is essentially a reaction vessel. (3-5 mL volume) equipped with a heater to conduct the evaporation and solvent exchange processes. The azeotropic drying and the activation of fluoride ion typically require 20-30 minutes after the fluoride concentration step. The activated fluoride ions are then transferred into the capillary microreactor to perform the radiosynthesis. An example of such a radiosynthetic process is set forth in V. R. Bouvet, et al., *Synthesis of Hypoxia Imaging Cell* 1-(5-*deoxy*-5-*fluoro*-α-*D*-*arabinofuranosyl*)-2-*nitroimidazol Using Microfluidic Technology*, Nuc. Med. Biol., 38, 235 (2010), which is hereby incorporated herein in its entirety by reference.

This disclosure sets forth methods, including methods based on the preparation and utilization of functional polymer monoliths on microfluidic chip for rapid (radio)chemistry. Polymer monoliths are structures comprising a continuous bed of porous material possessing many flow-through pores that enable materials such as N analyte to flow at high rates, while still exhibiting a very high surface area and performances comparable with the traditional resins. Further examples of polymer monoliths are described in S. Xie, et al., *Porous Polymer Monoliths: Preparation of Sorbent Materials with High-Surface Areas and Controlled Surface Chemistry for High-Throughput, Online, Solid-Phase Extraction of Polar Organic Compounds*, Chemistry of Materials, 10, 4072 (1998), which is hereby incorporated herein in its entirety by reference.

In comparison to the conventional micron-sized resin, polymer monoliths have achieved distinctive performances over their packed column counterparts in various applications ranging from chromatography, separation, catalysis, solid phase synthesis, molecular recognition and decontamination. Specifically, the inherent features of polymer monoliths such as the high porosity, high surface area and high hydrodynamic flow are suitable for rapid concentration of the F18-fluoride ion from milliliter volumes to microliter volumes in a short time. This approach allows a simple design with minimal hardware, such as high pressure pumps and fittings to flow reagents at reasonable timescale for radiochemistry and chemistry applications. Utilizing polymer monoliths allows integration to existing flow through microreactor systems as well as provides streamlining flow-through in microfluidic platform for multistep synthesis (e.g. F18-radiochemistry). The new monolithic microfluidic platform can be used, for example, for ion preconcentration, solvent exchange, and ion activation processes.

The present disclosure also relates to the photo-irradiation of functional styrenic and methacrylate monoliths carrying reactive moieties such as vinylbenzyl chloride and glycidyl methacrylate on microfluidic devices or within polymer tubing. The photo-polymerization of the parent polymer monolith is optimized by varying the composition of the initiators, crosslinkers, porogens, monomers, and polymerization time to yield a monolith with high hydrodynamic flow. Methods described herein incorporating features of the present invention yields a polymer structure that has high trapping and releasing efficiencies in various environments, for example, in a glass microfluidic chip or within polymer micro-tubing.

Some embodiments incorporating features of the present invention, can concentrate volume ranging from milliliters to tens of microliters for subsequent chemical reactions on microfluidic devices. One can also pattern different phases of polymer monoliths (different functionalities) within a single microfluidic chip to realize a fully integrated platform or the concept of lab-on-a-chip based on the in situ photopolymerization of monoliths following the concept set forth by Frechet et al. [Mair, D. A., Schwei, T. R., Dinio, T. S., Svec, F., Frecher, J. M. J. Lab on Chip, 2009, 9, 877-883].

In some embodiments, the microfluidic channel is first activated to provide a covalent anchor for the polymer monoliths on the surface of the chip, such as by providing a vinyl coating thereon. The polymerization mixture is then flowed into the chip, followed by photo-irradiation at 470 nm for 45 minutes to obtain a benzyl chloride functionalized polymer monolith. The reactive benzyl chloride moieties are then functionalized with N-methyl imidazole (1 mM) at 90 degrees Celsius with a flow rate of 17 uL/min. [$^{18}$F]fluoride ion in water and THF mixture (500 µL) is then flowed through the imidazole monolith microchip at 33 µL/min. On-chip radiolabeling reaction is then performed by flowing mannose triflate in anhydrous acetonitrile at a flow rate of 17 µL/min while heating at 120 degrees Celsius.

In some embodiments a method of preparing a polymer monolith structure within a microfluidic chip for use in a multistep reaction comprises the steps of providing a microfluidic chip having flow channels, providing a mixture of one or more monomers, flowing said mixture of monomers through the microfluidic chip channels, subjecting the flowed mixture of monomers to irradiation such that the monomers polymerize to form a polymer monolith structure.

In some embodiments, a method of exchanging and activating fluoride ions on a flow through microfluidic chip, comprises the steps of providing a microfluidic chip, vinylizing the microfluidic chip to form and covalently anchor polymer monoliths in channels on or below the surface of said chip and flowing [$^{18}$F]Fluoride ion water through said monoliths on the chip and eluting the $^{18}$F fluoride ion via treatment with cryptands and potassium carbonate or potassium bicarbonate, or tetraalkylammonium bicarbonate.

In some embodiments, microfluidic chip for use in a multistep reaction comprises a base chip body portion, channels formed in said base chip body portion, and polymer monoliths formed within said channels.

These and other further features and advantages of the invention would be apparent to those skilled in the art from the following detailed description, taking together with the accompanying drawings, wherein like numerals designate corresponding parts in the figures, in which:

BRIEF DESCRIPTION OF THE DRAWINGS

FIG. 1A depicts a schematic representation of one embodiment of a method incorporating features of the present invention;

FIG. 1B is an enlarged representation of a flow channel in FIG. 1A;

FIG. 2A is a schematic representation of second embodiment of a method incorporating features of the present invention;

FIG. 2B is an enlarged image of a portion of a flow channel within a step of FIG. 2A;

FIG. 2C is an enlarged image of a portion of a flow channel in a second step of FIG. 2A;

FIG. 2D is a chemical formula of a compound within the step of FIG. 2B;

FIG. 2E is a chemical formula of a compound within the step of FIG. 2C;

FIG. 3 depicts a chemical reaction using one embodiment of a method incorporating features of the present invention;

FIG. 4 is a graphical representation of a comparison of fluoride-18 ion count with [$^{18}$F]FTAG according to the embodiment of FIG. 3;

FIG. 5 a schematic representation of one embodiment of a method incorporating features of the present invention FIG. 6 a chemical reaction using one embodiment of a method incorporating features of the present invention.

DETAILED DESCRIPTION

Figure 7:
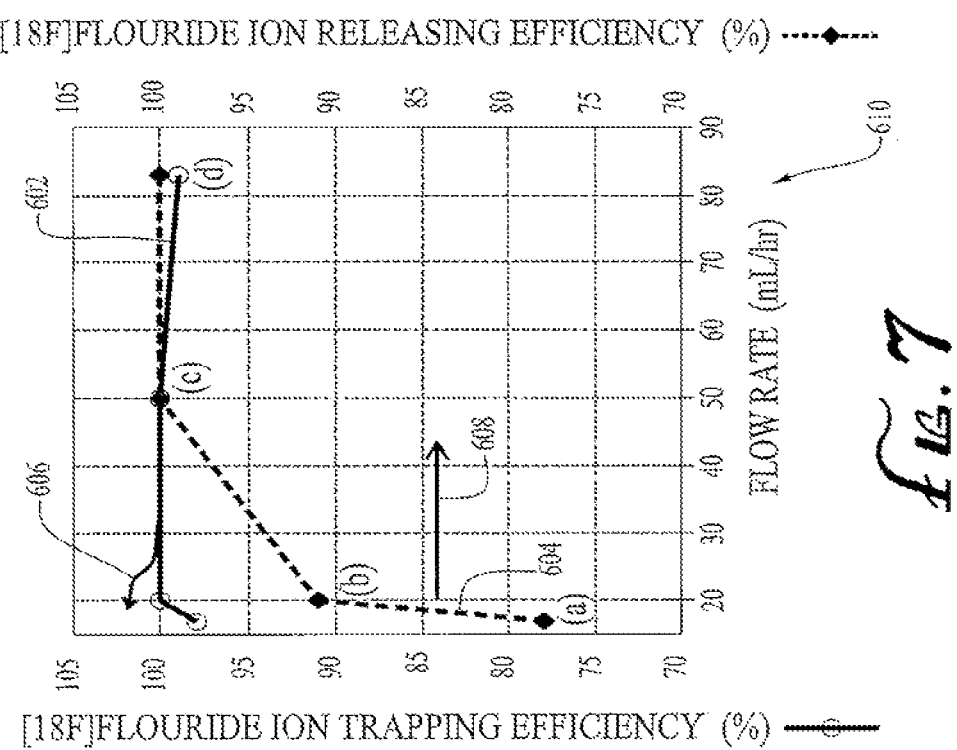
FIG. 7 depicts a graphical representation of the [$^{18}$F]fluoride ion trapping and releasing efficiency as a function of the flow rate through a monolith prepared using different UV polymerization times.

The present disclosure sets forth a first high-efficiency concept of integrating a functional polymer monolith on a flow through microfluidic platform to perform ion concentration, solvent exchange and activation processes within a single chip. Due to the difficulty in packing micron-sized beads onto or into microfluidic channels, this disclosure sets forth methods adapted to the in situ polymerization of functional monoliths within 150×150×52000 µm channels. Such channels can be formed on or within a microfluidic chip or any shape and size container, for example, on a base body portion of the chip. It is understood where the present disclosure discussed formation of channels in a chip it can include the channels being formed within the chip and/or on the chip. Polymer monoliths are uniquely suitable for microfluidic applications due to the ease of preparation, high loading capacity, high surface area, tunable pore size, tunable functionalities and high hydrodynamic flow. Conventional approaches are not suitable for utilization on microfluidic devices due to size limitation of resins, which leads to the difficulties in packing beads and frits (such as various vitreous substances, such as a mixture of silica and fluxes, utilized in the making of glass, porcelain, glazes, or enamels) within the confined microchannels and the limited loading capacity of the reactive substrates.

The present disclosure sets forth a reliable methodology for the preparation of polymer support with high surface area and high hydrodynamic flow for concentrating a dilute radioactive source (~1000 µL) by 20-fold (to ~50 µL). Methods according to the present disclosure confirm that the anion exchange monoliths polymerized within 13 µL serpentine channels of a microfluidic chip comprised sufficient surface area to trap up to 1 Curie (Ci) in radioactivity of [$^{18}$F]fluoride ions. These finding were based on the theoretical specific activity of [$^{18}$F]fluoride ion obtained through the [18O]H$_2$O (p, n) reaction, wherein an equivalent number of moles of potassium fluoride (µmoles) were added to the initial. [$^{18}$F]fluoride/[18O]H$_2$O solution). This example result overcomes the limitations in prior art methods (such as those cited above), in which a maximum of only 500 µCi of [$^{18}$F]fluoride ions were trapped on anion exchange resins packed within Polydimethylsiloxane (PDMS) microchannels.

Furthermore, the present disclosure discloses methods which enable the release of [$^{18}$F]fluoride ions with high efficiency from monolithic chips in an activated form for subsequent chemical synthesis. For example, to achieve high release and high fluorination efficiency, varying phase transfer catalysts, bases, concentrations of bases, solvent, water to organic solvent content, and temperature were investigated. In some embodiments, an optimal condition was to elute the trapped fluoride with 65 mM Kryptofix and 25 mM K$_2$CO$_3$ in MeCN with 0.5% water.

Throughout this disclosure, the preferred embodiments herein and examples illustrated are provided as exemplars, rather than as limitations on the scope of the present disclosure. As used herein, the terms "invention," "method," "system," "present method," "present system" or "present invention" refers to any one of the embodiments incorporating features of the invention described herein, and any equivalents. Furthermore, reference to various feature(s) of the "invention," "method," "system," "present method," "present system," or "present invention" throughout this document does not mean that all claimed embodiments or methods must include the referenced feature(s).

It is also understood that when an element or feature is referred to as being "on" or "adjacent" another element or feature, it can be directly on or adjacent the other element or feature or intervening elements or features that may also be present. Furthermore, relative terms such as "outer", "above", "lower", "below", and similar terms, may be used herein to describe a relationship of one feature to another. It is understood that these terms are intended to encompass different orientations in addition to the orientation depicted in the figures.

Although the terms first, second, etc. may be used herein to describe various elements or components, these elements or components should not be limited by these terms. These terms are only used to distinguish one element or component from another element or component. Thus, a first element or component discussed below could be termed a second element or component without departing from the teachings of the present invention. As used herein, the term "and/or" includes any and all combinations of one or more of the associated list items.

The terminology used herein is for the purpose of describing particular embodiments only and is not intended to be limiting of the invention. As used herein, the singular forms "a," "an," and "the" are intended to include the plural forms as well, unless the context clearly indicates otherwise. For example, when the present specification refers to "a" transducer, it is understood that this language encompasses a single transducer or a plurality or array of transducers. It will be further understood that the terms "comprises," "comprising," "includes" and/or "including when used herein, specify the presence of stated features, integers, steps, operations, elements, and/or components, but do not preclude the presence or addition of one or more other features, integers, steps, operations, elements, components, and/or groups thereof.

Embodiments of the invention are described herein with reference to different views and illustrations that are schematic illustrations of idealized embodiments of the invention. As such, variations from the shapes of the illustrations as a result, for example, of manufacturing techniques and/or tolerances are expected. Embodiments of the invention should not be construed as limited to the particular shapes of the regions illustrated herein but are to include deviations in shapes that result, for example, from manufacturing.

In comparison to the fluoride concentration and activation methodologies reported for macroscale systems, such as those discussed above, utilizing a microfluidic platform as disclosed herein can effectively release fluoride ions in a much smaller volume (500 µL in the macrosystem versus 20-50 µL in the presently described procedure). Such microfluidic platforms can be integrated with any typical microfluidic synthesizer (batch mode and continuous-flow mode), while the existing technologies based on beads and resins cannot be easily miniaturized and automated. An existing technology of anion exchange technology for microfluidic application is disclosed by Elizarov et al., in which fluoride trapping efficiency (>95%) could be achieved in a 2 µL bed volume of resin. This cartridge, which was resins packed within polyethylene tubing, traps ~800 mCi of radioactive source from the cyclotron in as little as 5 µL volume. However, some embodiments of methods described herein do not include the fluoride activation step, which necessitates the drying and activation process to be performed on or off the chip.

In some embodiments, the anion exchange polymer monoliths are photo-polymerized directly within the channels of a glass microfluidic chip (for example, FC_R150.696; Micronit) with dimensions 150 µm×150 µm×52,000 µm and a total volume of 13 µL. The glass channels of the microfluidic chip are first activated with methacryloxypropyltrimethoxysilane according to procedures in the literature. Briefly, NaOH (1 M; 1 mL) is flowed by hand through the empty glass channels using a 1 mL syringe, followed by HCl (1M; 1 mL) and finally washed with water (1 mL) to preactivate the chip. The pre-activated microfluidic chip is then dried in a vacuum oven overnight at 80° C. The channels are then flowed with the methacryloxypropyltrimethoxysilane (0.31 g; 1.3 mM; 0.3 mL) solution in acetone (3:7 v/v), and let sit in darkness at room temperature overnight. The excess alkoxysilane reagent is washed with copious amount of acetone and the channels are air dried.

In some embodiments, the polymerization mixture contains one or more of a photoinitiator, photosensitizer, reactive monomer, crosslinker and porogens. The in situ polymerization of poly (vinylbenzylchloride-co-vinylbenzene) was carried out using published procedure with slight modification. Such published procedure can be found, for example, in Z. Walsh, et al., Visible Light Initiated Polymerization of Styrenics Monolithic Stationary Phases Using 470 nm Light Emitting Diode Arrays. J. Sep. Sci., 33, 61 (201) which is hereby incorporated herein in its entirety by reference. A mixture of S-camphorquinone (2.4 mg; 0.14 mmols), ethyl-N-dimethylbenzoate (32 mg; 0.16 mmols), N-methyl-pyridinium tetrafluoroborate (32 mg; 0.18 mmols) is dissolved in a mixture of acetonitrile (237 µL), isopropanol (500 µL) and 1-decanol (600 µL). The mixture is mixed thoroughly using a vortex to obtain a bright clear yellow solution. The 4-vinylbenzylchloride and divinylbenzene monomers and crosslinkers are then filtered through neutral alumina oxide prior to use. Vinylbenzyl chloride (500 µL; 508 mg; 3 mmol) and divinylbenzene (250 µL; 230 mg; 1.8 mmols) are added to the yellow mixture and then bubbled with argon for 5 minutes to remove oxygen.

In some embodiments, the deoxygenated mixture is then added into a microfluidic chip using a pump mechanism, such as a syringe, and the inlets/outlets are plugged. The chip is then placed between three panels of LED light arrays (450 nm; 12×20 mW at 4.2 A, 3.7V) at a distance of 0.5 cm for a predetermined amount of time. In some embodiments a preferred polymerization condition is to first turn on the LED light source for an hour to allow for equilibration and consistency from day to day production. Visible-light polymerization on a microfluidic chip is conducted for 40 minutes, and the chip is immediately washed with tetrahydrofuran (THF; 5 mL) to remove any unreacted monomers and crosslinkers.

In some embodiments, the functionalization of the reactive benzyl chloride moiety is then performed by dissolving the N-methyl imidazole (0.082 g; 1 mmols) in acetonitrile or Tetrahydrofuran (THF) (5 mL). The mixture is flowed at 0.5 mL/hour through the microfluidic chip containing the poly (vinylbenzylchloride-co-divinylbenzene) monoliths prepared as described previously. The microfluidic chip is heated at 80° C. to complete the functionalization reaction. The extent of the functionalization reaction can be qualitatively evaluated via a calorimetric test. Such a calorimetric test is set forth in F. Galindo, et al, *A Sensitive Colorimetric Method for the Study of Polysterine Merrifield Resins and Chloromethylated Macroporous Monolithic Polymers*, J. Comb. Chem., 6, 859 (2004), which is hereby incorporated herein in its entirety by reference. Briefly, 4-(4-nitrobenzyl)pyridine (NBP) (53 mg; 0.25 mmols) is dissolved in 5 mL solution of dichloromethane/dimethylformamide (1:1, v/v) with 5% triethylamine. The resulting clear solution is then flowed through the monoliths. The monoliths will typically develop a color ranging from pink to violet, depending on the amount of unreacted benzylchloride moieties.

Under the preferred functionalization condition described above, the monolith remains yellow in color after the colorimetric test, which confirms that the functionalization reaction went to completion. A controlled experiment can be conducted by utilizing the un-functionalized poly (vinylbenzylchloride-co-divinylbenzene) monolith, in which an intense purple color will appear in 30-60 mins. After the functionalization reaction, the excess reagent can be washed with THF (10 mL) at 1 mL/hr flow rate using a syringe pump.

Quaternary ammonium anion exchange monolith Glycidyl methacrylate, ethylene glycol dimethacrylate, azobisisobutyronitrile and porogens are then bubbled with argon for five minutes. The polymerization mixture is then flowed into varying lengths of Polytetrafluoroethylene (PTFE) tubing (inner diameter: 750 µm; (3 to 25 cm)), and the two ends are plugged. PTFE is also commonly known by its trade-name Teflon®, which is a trademark of E.I. du Pont de Nemours and Company. PTFE tubing is cheap, stable against a wide range of organic solvents, flexible and easy to configure and thus is suitable for various applications. Due to the chemical inertness of the majority of PTFE tubing, installation of chemical functionalities for subsequent chemistry within the walls of Teflon tubing has not been widely studied. Different varieties of PTFE tubing can be utilized with methods according to the present disclosure. For example, ethylenetrifluoroethylene (ETFE) tubing can be utilized as will be discussed further below.

The filled PTFE tubing was then placed into an Electrocure 500 UV flood-curing chamber with 365 nm UV lamp and at 30 mW/cm$^2$ power output. The polymerization times can be varied from 3 to 10 minutes. UV polymerization time of 7, 9 and 10 minutes were found to be suitable. One of the most preferred polymerization conditions consists of a 60:40 monomer/crosslinker ratio (v/v) and a 33.3:66.6 monomers/porogens (v/v) solution. After the UV polymerization, the reactive glycidyl methacrylate monoliths are functionalized with 5% trimethylammonium hydrochloride salt (aq) by flowing at 0.6 mL/hr through the monolith placed in an oil bath at 80° C. for 10 hours. The backpressure of the monolith increases by several factors (1-3×) under the preferred polymerization and functionalization conditions. After the functionalization, the monoliths were then washed with 10 ml of water, 10 ml of 1N HCl, and then copious amounts of water at a flow rate of 33 mL/hr. Table 1 shows optimization of the in situ polymerization of glycidyl methacrylate and ethylene glycol dimethacrylate in different porogens (pores forming solvent) system. The flow rate measurement is an indirect indication of the hydrodynamic flow of each polymer monolith as a function of the porogen system.

TABLE 1

| POROGENS | UV (mins) | HIGHEST FLOW RATE |
|---|---|---|
| 80% MeOH; 20% EtOAc | 3 | 0.1 |
| 80% MeOH; 20% EtOH | 3 | 0.5 |
| 80% MeOH; 20% Hexanes | 2 | 0.5 |
| 80% MeOH; 10% EtOAc; 10% Hexanes | 3 | 0.5 |
| 90% MeOH; 10% EtOH | 3 | 0.2 |
| 890% MeOH; 10% EtOAc | 3 | 0.3 |

The porogen system which resulted in the least backpressure is 80:20 methanol/ethanol (v/v). The backpressure measurements were obtained using a high-performance liquid chromatography (HPLC) pump flowing at 0.1 mL/min through different polymer monoliths prepared at varying polymerization times (or UV irradiation times). Table 2 shows backpressure measurement obtained from the HPLC pump flowing at 0.1 mL/min through different polymer monolith prepared at varying polymerization time (or UV irradiation time).

TABLE 2

| POROGENS | UV (mins) | BACK PRESSURE psi/cm |
|---|---|---|

For the fluoride ion trapping protocol, 50:50 (v/v) of the [$^{18}$F]fluoride ion/[18O]H$_2$O and THF is mixed and then flowed through the poly(imidazolium cation) monoliths at a flow rate of 50 µL/hr. The average trapping efficiency under this condition is 98±2% (n=5) over different microfluidic chip and over multiple days of experiments. The polymer monolith can typically be reused over multiple times, without compromising on the trapping and releasing performances. The trapped [$^{18}$F]fluoride ion is then washed with acetonitrile (200 µL) to remove any residual water. Finally, the [$^{18}$F] fluoride is eluted with a mixture of Kryptofix (K$_{2.2.2}$) (93 mM) and potassium carbonate (25 mM) in 99.5:0.5 MeCN/H$_2$O (v/v) with an average released efficiency of 82±2% (n=6). For subsequent batch fluorination reactions on a PTFE-coated glass substrate, the [$^{18}$F]KF/K$_{2.2.2}$ released from the monolithic microfluidic chip can be directly mixed with a solution of mannose triflate in DMSO (100 mM), and heated at 120° C. for 10 minutes. For radiofluorination on a continuous flow glass microfluidic chip, 20 µL of the [$^{18}$F] KF/K$_{2.2.2}$ can be diluted in 100 µL of mannose triflate (100 mM) in DMSO (20 µL). The mixture can then be flowed through an empty glass microfluidic chip at a flow rate of 10 µL/min and heated at 150° C.

An optimization comparison of different [$^{18}$F]fluoride releasing conditions using varying phase transfer catalysts, bases, and solvents is shown in Table 3, which shows Optimization of different [$^{18}$F]fluoride releasing conditions using varying phase transfer catalysts, bases, and solvents to achieve the high trapping and releasing efficiencies from the monolithic microfluidic. The most optimal condition is in using the Kryptofix and potassium carbonate complex in 99.5:0.5 MeCN/H$_2$O composition (bolded; last row).

TABLE 3

| Trapping Eff. (%) | Release Eff. (%) | Base | [Base] (mM) | Solvent (ratio v/v) |
|---|---|---|---|---|
| 93 | 12 | NEtyl$_4$HCO$_3$ in CH3CN | 5 mM in CH3CN | CH3CN |

TABLE 3-continued

| Trapping Eff. (%) | Release Eff. (%) | Base | [Base] (mM) | Solvent (ratio v/v) |
|---|---|---|---|---|
| 89 | 67 | TBAF in CH3CN | 100 mM in CH3CN | CH3CN |
| 96 | 97 | NEtyl4HCO3 in 1:1 ratio of THF:H2O | 5 mM in CH3CN | CH3CN |
| 77 | 16-23 | NEtyl4HCO3 in THF, (1 mL) CH3CN | 0.7 mM in CH3CN | CH3CN 0.02% water |
| 55 | 9.5 | NEtyl4HCO3 CH3CN | 5 mM in CH3CN | CH3CN Thexyl-OH |
| 18 | 3.5 | — | — | Thexyl-OH (3:1) |
| 18 | 3.8 | NEtyl4HCO3 CH3CN | 10 mM in CH3CN | Thexyl-OH (3:1) |
| 18 | 4 | NEtyl4HCO3 CH3CN | 10 mM in CH3CN | Thexyl-OH (3:1) |
| 98 | 77 | $K_{2.2.2}$/$K_2CO_3$ | 25 mM | MeCN/$H_2O$ (v/v 99.5:0.5) |

For a fluoride ion trapping and releasing method using a quaternary ammonium polymer monolith, [$^{18}$F]fluoride ion/[18O]$H_2O$ is flowed through the glycidyl methacrylate monoliths at a flow rate of 1 ml/hr. The average trapping efficiency under this condition is 99.9±0.15% (n=6) over different monoliths and over multiple trials. The trapped [$^{18}$F] fluoride ions were eluted with 1 M $K_2CO_3$ (aq) at 3 ml/hr. The average releasing efficiency under this condition is 96.2±5.0% (n=8). The eluting volume is between 30-150 ul, which is suitable for application on microfluidic devices (typical microreactor volume being 5-20 μL). Quantitative trapping and releasing efficiencies are found at a flow rate of 0.5 mL/hr and up to 5 mL/hr.

Upon releasing the radioactive [$^{18}$F]fluoride ion using 1 M $K_2CO_3$ (aq, the cartridge can be re-conditioned with 1 ml of $KHCO_3$ (1 M), followed by 1 ml of water. Based on this reconditioning methodology, the anion exchange polymer monolith can be used over multiple trapping and releasing processes without diminishing their performances.

In some embodiments, a method to prepare a imidazolium polymer monolith on a glass microfluidic chip can utilize ETFE tubing, for example, ETFE tubing containing C—H moieties to provide a polymerizable anchor within the walls of the tubing. This step provides the advantage of ensuring complete filling and ensuring that the polymer bed is covalently anchored to the tubing. The functionalization of the ETFE tubing can be modified according to the literature procedure reported for the functionalization of polyvinylidine fluoride (PVDF) membrane. (See S. Xie, et al., *Porous Polymer Monoliths: Preparation of Sorbent Materials with High-Surface Areas and Controlled Surface Chemistry for High-Throughput, Online, Solid-Phase Extraction of Polar Organic Compounds*, Chemistry of Materials, 10, 4072 (1998), incorporated by reference above).

For example, Benzophenone (0.25 g; 1.4 mM) and EDMA (0.1 g; 0.5 mmoles; 95 uL) was dissolved in 5 mL of acetone to achieve a final concentration of 0.1 M of ethylene glycol dimethacrylate (EDMA) and 5% of benzophenone in acetone. The reaction mixture is then sonicated in a Scintillation vial for ~5 minutes. The degassed mixture is then immediately charged into the ETFE tubing using a pump mechanism, such as a syringe, and capped. The tubing is then placed into the UV spectrolinker with 254 nm lamp at 504 mJ/for 20 min. After the initial photografting step, the tubing is then washed with ~1 mL of acetone and briefly dried with air.

Next, a polymerization reaction to generate poly (vinylbenzylchloride-co-divinylbenzene) monolith was carried out using published procedure with slight modification. Such published procedure can be found, for example, in Z. Walsh, et al., Visible Light InitiatedPolymerization of Styrenics Monolithic Stationary Phases Using 470 nm Light Emitting Diode Arrays. J. Sep. Sci., 33, 61 (2011) which is hereby incorporated herein in its entirety by reference. Initiator solution is prepared with 6.4 mg (0.0386 mmol) S-(+)-camphorquinone, 32 mg (0.165 mmol) ethyl-4-dimethylamino benzoate and 32 mg (0.172 mmol) N-methoxyphenylpyridinium tetrafluoroborate were dissolved in 250 μL of acetonitrile, 500 μL of 1-propanol and 600 μL. 350 μL ((2.49 mmol) of vinylbenzyl chloride and 350 μL ((2.46 mmol) of divinylbenzene were mixed with the initiator solution and sonicated for 20 minutes.

EDMA functionalized ETFE tubing (400 μm inner diameter) was then filled with the above solution using a pump mechanism, such as a syringe, and sealed. The sealed tubing was then placed between two arrays of 470 nm LED light source (12×20 mW at 4.2 A, 3.7V) at 1 cm apart in a closed box for two and half hours. White solid formed in the tubing, was washed thoroughly with copious amount of acetonitrile. The typical length of ETFE tubing used for such a polymerization reaction was approximately 30 cm in length. The poly (vinylbenzylchloride-co-divinylbenzene) in ETFE tubing and microfluidic chip was functionalized by flowing 2 mL of 0.2 M N-methyl imidazole solution through the microchannels at 100° C. with a flow rate of 0.1 mL/hour. The ETFE tubing was then wrapped with aluminum foil to assure heating from all sides of the ETFE tubing and placed on a hotplate for heating treatment.

Regarding the trapping of [$^{18}$F]Fluoride on PS-Im$^+$Cl$^-$ in the Microfluidic chip, [$^{18}$F]Fluoride from the cyclotron was first diluted with a mixture of a 1:1 ratio of THF and water with potassium fluoride (0.3 mM). 200 μL of this solution was then flowed through the imidazolium monolith in the microfluidic chip using a pump, such as a syringe, at flow rate of 1-10 mL/hr. The trapping efficiency on the microfluidic chip using the 1:1 ratio of THF and water is 96±4& (n=13). Regarding the trapping of [$^{18}$F]Fluoride on the imidazolium monolith in ETFE tubing, [$^{18}$F]Fluoride from the cyclotron was first diluted with water that was doped with potassium fluoride to correspond to the amount of F-18 present in 1 Ci of activity in 200 μL (0.3 mM). This solution was then flowed at 100-250 μL/min through 5 cm ETFE tubing containing PS-Im$^+$Cl$^-$ monolith. The trapping efficiency on fluoride-18 ion in water on the ETFE in water was found to be 97%±4 (n=39).

Regarding the general methodology for fluoride ion concentration, release and radiofluorination reaction, the imidazolium polymer monolith on the ETFE tubing was connected to an empty glass microfluidic chip (dimension: 150 μm×150 μm×52000 μm; volume=13 μL) via a ETFE tubing with an inner diameter of 250 μm. Using a pump, such as a syringe, the mixture of precursor, base and phase transfer catalyst was flowed at 10-100 μL/min through the imidazolium monolith and the glass microfluidic chip was preheated at 120° C. The concentration of precursor, base and phase transfer catalyst for each precursor are outlined in Table 4 along with their fluorination and radioactivity releasing efficiencies along with the number of experiments (n). After the reaction, another 200 μL of solvent was passed through the polymer monolith and the microfluidic chip to collect all of the products and remaining starting material. The combined product mixture was analyzed via radio-TLC.

Table 4 shows example reaction conditions for releasing the fluoride-18 ion followed by the radiofluorination reaction on an empty microfluidic chip using different precursors. The radiolabeled product formed on radio-TLC. The ratio of the crude radiolabelled product to the amount of radioactivity trapped on the monolith gives the final RCY.

TABLE 4

| Precursors | Base | Solvent | Precursor (mM) | Fluorination efficiency | R.C.Y | Releasing efficiency |
|---|---|---|---|---|---|---|
| [TsO-propyl-dimethoxybenzamide-pyrrolidine-allyl precursor] | 25 mM $K_2CO_3$/Kryptofix | MeCN, 0.5% $H_2O$ | 39 | 73 ± 4, n = 3 | 65 ± 7, n = 3 | 91 ± 10, n = 3 |
| [Ethyl 4-(trimethylammonio)benzoate triflate] | 25 mM $K_2CO_3$/Kryptofix | MeCN, 0.5% $H_2O$ | 48 | 79 ± 8, n = 4 | 41 ± 21, n = 4 | 39 ± 9, n = 4 |
| [DMTrO-nosylate-thymidine-Boc precursor] | 25 mM $NEthyl_4 HCO_3$ | 1:3 MeCN: Thexyl Alcohol | 54 | 93 ± 4, n = 3 | 44 ± 5, n = 3 | 50 ± 4, n = 3 |
| [Ethyl 4-(trimethylammonio)benzoate triflate] | 50 mM $KHCO_3$/Kryptofix | MeCN, 0.5% $H_2O$ | 47 | 96 ± 5, n = 3 | 64 ± 17, n = 3 | 89 ± 5, n = 3 |
| [Tetra-O-acetyl mannose triflate] | 25 mM $NEthyl_4 HCO_3$ | MeCN, 0.5% $H_2O$ | 48 | 93 ± 4, n = 3 | 78 ± 7, n = 3 | 84 ± 7, n = 3 |
| [DMTrO-nosylate-thymidine-Boc precursor] | 25 mM $KHCO_3$/Kryptofix | 1:3 MeCN: Thexyl Alcohol 0.5% $H_2O$ | 51 | 77 ± 3, n = 3 | 60 ± 3, n = 3 | 96 ± 2, n = 3 |

[$^{18}$F]F$^−$ releasing efficiency was measured by subtracting the amount of activity left on the PS-Im monolith from the amount of activity trapped on the PS-Im monolith. The fluorination efficiency was measured via radio-TLC. The radiochemical yield (RCY) was calculated based on the radioactivity collected in product vial multiply by the percentage of radiolabeled product formed on radio-TLC. The ratio of the crude radiolabelled product to the amount of radioactivity trapped on the monolith gives the final RCY.

Figures illustrating some of the above disclosed embodiments are be discussed below to further clarify methods according to the present disclosure. FIG. 1A depicts a schematic 100 showing an overview of a [$^{18}$F]fluoride ion source 102, which can be obtained from the cyclotron, being concentrated and activated on a monolithic flow through microfluidic chip 104 to yield the activated [¹⁸F]fluoride ion 106 for subsequent radiofluorination reaction, without performing additional drying steps. As discussed above, the monolithic microfluidic chip comprises a continuous bed of macroporous polymer functionalized with an anion exchange functionalities. This is better shown in an expanded view 108 of a portion of the microfluidic chip 104 (FIG. 1B).

FIG. 2A shows a schematic 200 depicting a representation of a method of preparing a poly(vinylbenzyl chloride-co-divinylbenzene) monolith within a microfluidic chip 202 with serpentine channels 204 on a chip. In this embodiment the dimensions of the serpentine channels are 150 µm×150 µm×52000 µm. In the method depicted, polymerization mixtures 206 are prepared as set forth above and flowed through the microfluidic chip 202 where they are subjected to a visible light irradiation step 208. This results in the formation of a vinylbenzochloride chemical structure 210 (FIG. 2D) which has a first topology 212 as depicted in FIG. 2B. This vinylbenzochloride chemical structure 210 is then functionalized in a functionalization step 214 utilizing the methods described above, for example by utilizing N-methyl imidazole 216 in acetonitrile or THF. The resulting poly(vinylbenzyl chloride-co-divinylbenzene) 218 monolith structure is formed within the microfluidic chip 204 and has a second topology 220 as depicted in FIG. 2C and FIG. 2E.

FIG. 3 depicts a schematic representation of the reaction 300 of the addition of a radiofluoride 302 to mannose triflate 304 using the [¹⁸F]fluoride ion that was concentrated and activated on a monolithic microfluidic platform based on the methodology described above. The results of this process are shown in the comparison graph 306 of FIG. 4 which compares fluoride-18 ion count with [¹⁸F]FTAG. In the embodiment depicted, the model reaction using mannose triflate showed comparable fluorination efficiency when compared to an established method, which involved 4-drying steps. The method depicted had an 84%±7% (n=3) efficiency as compared to the convention 4-drying step method having an 88%±7% (n=11) efficiency.

FIG. 5 depicts a schematic representation of the reaction 400 of the preparation of poly (glycidyl methacylate-co-divinylbenzene) in a polymer tube under UV irradiation as described above. As shown in the schematic 400, a polymerization mixture 402, containing initiator porogens 404, such as glycidyl methacrylate moieties, are placed into a polymer tube 406 and subjected to a UV irradiation step 408. In this embodiment the polymer tube has an inner diameter of 750µπl. After the UV irradiation step 408, the initiator porogens 404 have a topology 410. The initiator porogens 404 are then functionalized in a functionalization step 412 with trimethylamine hydrochloride 414 under flow through conditions in a hot oil bath, resulting in the formation of poly (glycidyl methaclate-co-divinylbenzene) 416.

FIG. 6 depicts a schematic representation of a chemical reaction 500 of the [¹⁸F]fluoride trapping, releasing and reconditioning using the quaternary ammonium polymer monolith as described in detail above. As mentioned above, [¹⁸F]fluoride ion 502 is flowed through the glycidyl methacrylate monolith 504 in a flow through step 506. During the trapping step 508, the [¹⁸F]fluoride is eluted with a mixture 510 of Kryptofix ($K_{2.2.2}$) and potassium carbonate 512 in 99.5:0.5 MeCN/$H_2O$ (v/v). For subsequent fluorination reactions, the [¹⁸F]KF/$K_{2.2.2}$ 514 released from the monolithic microfluidic chip can be directly mixed with a solution of mannose triflate in DMSO (100 mM), and heated at 120° C. for 10 minutes. For radiofluorination on a continuous flow glass microfluidic chip, 20 µL of the [¹⁸F]KF/$K_{2.2.2}$ can be diluted in 100 uL of mannose triflate (100 mM) in DMSO (20 µL). The mixture can then be flowed through an empty glass microfluidic chip at a flow rate of 10 µL/min and heated at 150° C.

FIG. 7 depicts a plot 600 of the [¹⁸F]fluoride ion trapping 602 (corresponding to the left side of the y-axis 606) and releasing 604 (corresponding to the right side of the y-axis 608) as function of the flow rate (corresponding the x-axis 610). The lines and points on the graph represent monoliths that were prepared at different UV polymerization times including 3 minutes (at point (a)), 3.5 minutes (at point (b)), 7 minutes (at point (c)) and 10 minutes (at point (d)). As shown in the stack plot 600, the preferred polymerization times are 7 and 10 minutes, in which nearly quantitative results for both trapping and releasing are achieved at much higher flow rate (83 µL/min).

Methods incorporating features of the present invention herein are describe above. These experiments showed that the polymer monolith platform described herein can be applicable in F18 radiosynthesis and can be applicable for multistep chemical synthesis in flow through microfluidic devices. The quaternary ammonium polymer monoliths in polymer tubing is efficient in trapping milliliters volume of [¹⁸F]fluoride ion (aq) directly from the cyclotron into microliters volume for chemistry on microfluidic devices.

Although the present invention has been described in detail with reference to certain preferred configurations thereof, other versions are possible. Embodiments of the present invention can comprise any combination of compatible features shown in the various figures, and these embodiments should not be limited to those expressly illustrated and discussed. Therefore, the spirit and scope of the invention should not be limited to the versions described above.

We claim:

1. A method of exchanging and activating fluoride ions on a flow through microfluidic chip, comprising the steps of:
   providing a microfluidic chip with one or more channels on or in the chip;
   vinylizing the microfluidic chip;
   forming and covalently anchoring a polymer monolith in the one or more channels, the polymer monolith comprising a poly (vinylbenzylchloride-co-divinylbenzene) monolith structure functionalized with N-methyl imidazole;
   flowing [¹⁸F]Fluoride ion water through the monolith in the one or more channels; and
   eluting the [¹⁸F]fluoride ion via treatment with cryptands and potassium carbonate or potassium bicarbonate, or tetraalkyarnmonium bicarbonate.

2. The method of claim 1, wherein the microfluidic chip comprises glass.

3. The method of claim 1, wherein the one or more channels are serpentine channels formed in the chip.

4. The method of claim 3, wherein the polymer monolith is within the one or more channels and the volume of the polymer monolith is at least 13 µL.

5. The method of claim 4, wherein the serpentine channels have a cross section of about 150 µm×150 µm and a length of about 52000 µm.

6. The method of claim 1, further comprising the step of performing on-chip radiolabeling by flowing a mixture of mannose triflate in anhydrous acetonitrile or DMSO through the monolith and heating the mixture.

7. The method of claim 1, wherein the step of forming and covalently anchoring polymer monoliths in the one or more channels comprises light initiated polymerization of a monomer.

8. The method of claim 7, wherein the polymer monolith is formed from a mixture comprising a photoinitiator, photosensitizer, monomers, crosslinker, and porogen.

9. The method of claim 1, wherein the polymer monolith traps at least 1 Curie (Ci) of [$^{18}$F] fluoride ions.

10. The method of claim 1, wherein the [$^{18}$F] fluoride ion is eluted with 4,7,13,16,21,24-hexaoxa-1,10-diazabicyclo-(8.8.8)-hexacosane and potassium carbonate in 99.5:0.5 (v/v) MeCN/H$_2$O.

11. The method of claim 1, wherein the [$^{18}$F]Fluoride ion water comprising a mixture of [$^{18}$F]Fluoride ion/[$^{18}$O]H$_2$O and THF.

12. The method of claim 11, wherein the mixture is pumped through the one or more channels at a rate of about 50 μL/hr.

13. A method of exchanging and activating fluoride ions on a flow through microfluidic chip, comprising the steps of:
   providing a microfluidic chip with one or more channels on or in the chip;
   forming a polymer monolith in the one or more channels, the polymer monolith comprising a poly (vinylbenzyl-chloride-co-divinylbenzene) monolith structure functionalized with N-methyl imidazole;
   flowing [$^{18}$F]Fluoride ion water through the monolith structure in the one or more channels; and
   eluting the [$^{18}$F]fluoride ion via treatment with a cryptand and a carbonate or bicarbonate.

14. The method of claim 13, further comprising the step of performing on-chip radiolabeling by flowing a mixture of mannose triflate in anhydrous acetonitrile or DMSO through the monolith structure and heating the mixture.

15. A method of exchanging and activating fluoride ions on a flow through microfluidic chip, comprising the steps of:
   providing a microfluidic chip with one or more channels on or in the chip;
   forming a polymer monolith in the one or more channels, the polymer monolith comprising a glycidyl methacrylate monolith structure functionalized with trimethylammonium hydrochloride salt;
   flowing [$^{18}$F]Fluoride ion water through the monolith structure in the one or more channels; and
   eluting the [$^{18}$F]fluoride ion via treatment with a cryptand and a carbonate or bicarbonate.

16. The method of claim 15, further comprising the step of performing on-chip radiolabeling by flowing a mixture of mannose triflate in anhydrous acetonitrile or DMSO through the monolith structure and heating the mixture.

17. The method of claim 15, wherein the eluting volume is between 30-150 μL.

* * * * *